United States Patent [19]

Kuroya et al.

[11] Patent Number: 5,166,233
[45] Date of Patent: Nov. 24, 1992

[54] FILM APPLICABLE TO ORAL MUCOSA AND DRUG PREPARATION COMPRISING THE SAME

[75] Inventors: Takamasa Kuroya; Yuichi Inoue, both of Osaka, Japan

[73] Assignees: Nitto Denko Corporation; Sunstar K.K., both of Osaka, Japan

[21] Appl. No.: 473,069

[22] Filed: Jan. 31, 1990

[30] Foreign Application Priority Data

Jan. 31, 1989 [JP] Japan .................................. 1-23306

[51] Int. Cl.$^5$ .......................... C08J 3/21; C08L 1/08
[52] U.S. Cl. ....................................... 524/37; 524/42; 524/43; 524/44; 427/2; 427/3
[58] Field of Search .............. 524/37, 42, 43, 44; 427/2, 3

[56] References Cited

U.S. PATENT DOCUMENTS

3,524,828  8/1970  Keithly .................................. 524/44

FOREIGN PATENT DOCUMENTS

0106107  4/1984  European Pat. Off. .
0200508  12/1986  European Pat. Off. .
0241179  10/1987  European Pat. Off. .
0275550  7/1988  European Pat. Off. .
1068786  11/1959  Fed. Rep. of Germany .

OTHER PUBLICATIONS

Chemical Abstracts, vol. 83, Mar. 1975, p. 373, Abstract No. 103302t.
Chemical Abstracts, vol. 99, No. 22, Nov. 1983, p. 349, Abstract No. 181420z.

Primary Examiner—Nathan M. Nutter
Assistant Examiner—Jeffrey Culpeper Mullis
Attorney, Agent, or Firm—Sughrue, Mion, Zinn, Macpeak & Seas

[57] ABSTRACT

A soft film applicable to the oral mucosa and a drug preparation comprising said film are disclosed, the film comprising a homogeneous mixture comprising a vinyl acetate homopolymer, an acrylic acid polymer, and a cellulose derivative capable of being dissolved in or swollen with water and a lower alcohol. The film or preparation is less causative of an adverse feeling on application to the oral mucosa, excellent in shape retention on water absorption, and adhesive to the oral mucosa for an extended period of time.

9 Claims, 1 Drawing Sheet

FILM APPLICABLE TO ORAL MUCOSA AND DRUG PREPARATION COMPRISING THE SAME

BACKGROUND OF THE INVENTION

A. Field of the Invention

This invention relates to a film which is applied to the wet mucosa of the oral cavity and a preparation comprising the same, which are useful to maintain a long-term intraoral administration of a drug.

B. Description of the Related Art

Known dosage forms for intraoral administration of drugs include solutions, ointments, troches, buccal tablets, sublingual tablets, etc. Recently, slow-releasing intraoral tablets of track-field type which are less causative of an adverse feeling in the oral cavity (as described in JP-A-55-59-09, JP-A-58-154547, and JP-A-58-154548, the term "JP-A" as used herein means an "unexamined published Japanese patent application") and slow-releasing Nifedipine tablets of track-field type applied to the oral mucosa (as described in JP-A-61-15829 and JP-A-61-17510) have been proposed. For the purpose of further reducing an adverse feeling in the oral cavity, medical bandage using, as a base, a water-soluble high polymer which exhibits adhesion when dissolved or gelled with water (as described in JP-A-60-142927), preparations applicable to the oral mucosa comprising a water-soluble film having incorporated thereinto a steroid or non-steroid agent (as described in JP-A-61-280423), and sheet preparations comprising a support sheet having thereon a drug, gelatin, agar, gluten, a carboxyvinyl polymer, a polyhydric alcohol, a gum, and a wax as essential components (as described in JP-A-61-85315) have also been proposed.

More recently, there have been proposed bases for application to the oral mucosa which comprise a mixture of a water-soluble substance and a water-insoluble substance; for example, intraoral bandage composed by a soft film in which at least one of a polycarboxylic acid and a polycarboxylic acid anhydride, and a vinyl acetate polymer are mixed in a compatible state as disclosed in JP-A-61-249472 and JP-A-61-249473; a base comprising a water-insoluble or sparingly water-soluble support having thereon an adhesive layer containing an acrylic acid polymer which exhibits adhesion when dissolved in or swollen with water and a water-insoluble cellulose derivative as disclosed in JP-A-63-160649; a composite for application to the oral mucosa comprising a surface layer containing ethyl cellulose and a vinyl-pyrrolidone polymer or copolymer having thereon an adhesive layer as disclosed in JP-A-63-171564 and JP-A-63-171565; and an adhesive composition containing a vinylpyrrolidone polymer or copolymer, at least one of hydroxyethyl cellulose and hydroxypropyl cellulose, and a water-retaining softener as disclosed in JP-A-63-174660.

However, none of these known intraoral preparations or bases satisfies both duration of adhesion and freedom from an adverse feeling in the oral cavity on use. For example, since solutions, ointments or the like preparations easily run away with saliva or other water content, it is difficult to maintain efficacy for a long time with these preparations. Troches, which are large tablets prepared by punching a mixture of a drug and a base, e.g., saccharides, cause a considerable adverse feeling. Buccal tablets and sublingual tablets are generally designed for rapid mucosal absorption of drugs and are, therefore, of short duration. The track-field type tablets, though slowly releasing a drug, have a thickness as large as 1.3 to 3 mm and lack softness, still involving the problem of an adverse feeling on use. The preparations for application to the oral mucosa comprising a water-soluble film containing a drug have softness and thereby cause a reduced adverse feeling in the oral cavity. However, since the film base is water-soluble, it is easily dissolved in saliva or water contents in the oral cavity and is, therefore, poor in duration of efficacy. The bases comprising a mixture of a water-soluble substance and a water-insoluble substance are soft and less causative of an adverse feeling upon use. Also, they take time to disappear in the oral cavity and are thus expected to have a longer duration of pharmaceutical effects as compared with bases comprising a water-soluble substance alone. These bases nevertheless exhibit adhesion only for 2 to 10 hours at the longest.

Hence, an intraoral preparation satisfying all the three requirements, i.e., freedom from an adverse feeling in the oral cavity on use, excellent shape retention on water absorption, and long-term adhesion to the wet oral mucosa, has not yet been developed.

SUMMARY OF THE INVENTION

An object of this invention is to provide a film applicable to the oral mucosa, which is less causative of an adverse feeling in the oral cavity on use, excellent in shape retention on water absorption, and adhesive to the oral mucosa for an extended time.

Another object of this invention is to provide a preparation applicable to the oral mucosa which comprises the above-described film and a drug as an active ingredient.

Other objects and effects of the present invention will be apparent from the following description.

The inventors have conducted a series of studies about a base which is less causative of an adverse feeling on application to the oral cavity, excellent in shape retention on water absorption, and adhesive to the oral mucosa for an extended period of time. As a result, it has been found that a film applicable to the oral mucosa satisfying all these requirements is obtained by using a homogeneous mixture comprising (A) a vinyl acetate homopolymer, (B) an acrylic acid polymer, and (C) a cellulose derivative capable of being dissolved in or swollen with water and a lower alcohol (hereinafter simply referred to as cellulose derivative), thus reaching the present invention.

The present invention relates to a soft adhesive film applicable to the oral mucosa comprising a homogeneous mixture comprising (A) a vinyl acetate homopolymer, (B) an acrylic acid polymer, and (C) a cellulose derivative capable of being dissolved in or swollen with water and a lower alcohol.

The present invention further relates to a composite film applicable to the oral mucosa comprising the above-described soft adhesive film having laminated on one side thereof a soft water-insoluble support film.

The present invention still further relates to a preparation comprising the above-described soft adhesive film containing a topical drug.

DETAILED DESCRIPTION OF THE INVENTION

Figure 1:
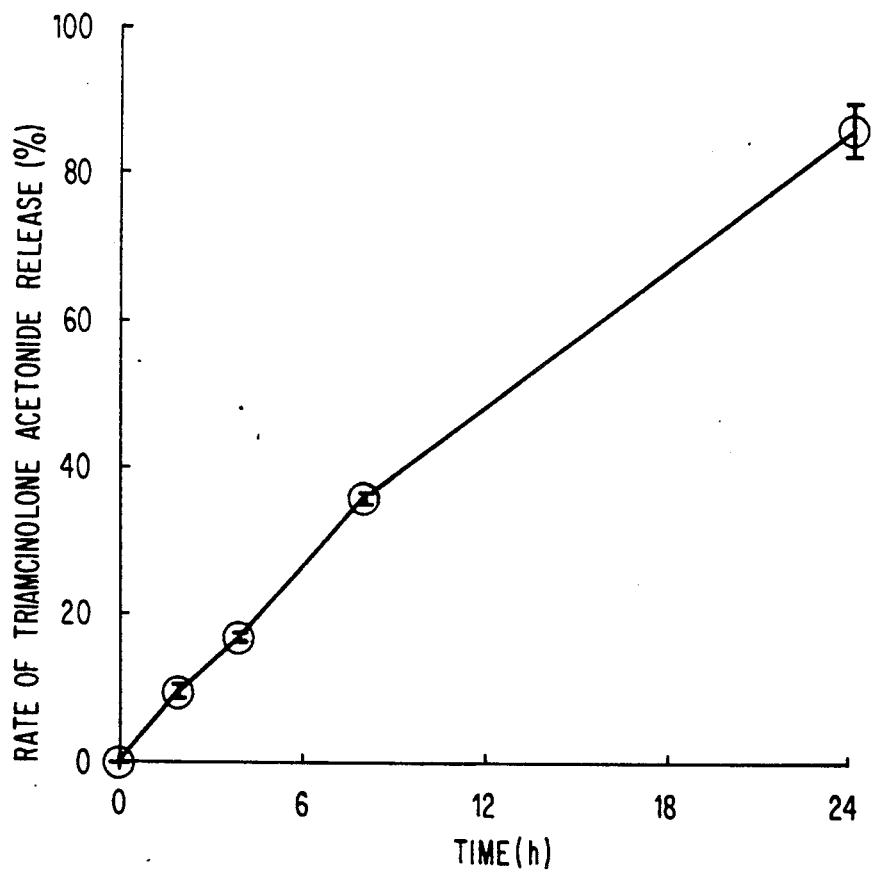
FIG. 1 illustrates the relationship of the rate of Triamcinolone Acetonide release to the time.

When the soft adhesive film according to the present invention is applied to, for example, the fore gingiva of the upper jaw, the adhesive film base absorbs saliva and a water content in the oral cavity to exhibit adhesion to the oral mucosa. The adhesiveness is retained for a long period of time because of the excellent shape retention. Since the film base is homogeneous and soft, it is tightly adhered to the oral mucosa without causing an adverse feeling during application. The terminology "homogenous" as used herein means that the vinyl acetate homopolymer, the acrylic acid polymer and the cellulose derivative in the mixture are homogeneously mixed under optical microscopic observation and that each of these components does not exist solely in parts.

The film according to the present invention is obtained using a homogeneous mixture of a vinyl acetate homopolymer, an acrylic acid polymer, and a specific cellulose derivative. A two-component mixture comprising only the vinyl acetate homopolymer and the acrylic acid polymer forms a homogenous soft film but is swollen with saliva or other water content in the oral cavity and is inferior in shape retention on application to the oral mucosa. Further, a two-component mixture comprising only the acrylic acid polymer and the cellulose derivative forms a homogeneous soft film but does not withstand long-term use in the oral cavity because of water-solubility of these components. Furthermore, a two-component mixture comprising only the vinyl acetate homopolymer and the cellulose derivative hardly forms a homogeneous and soft film.

The vinyl acetate homopolymer which can be used in the present invention is not particularly limited, and any known vinyl acetate homopolymer (as disclosed, e.g, in S. Imoto, *Plastic Zairyo Koza* (Lectures on Plastic Materials) Vol.14 Vinyl Acetate Resins, published by Nikkan Kogyo Press, Japan, on May 15, 1970) can be used as such either alone or in combination thereof. The weight average molecular weight of the vinyl acetate homopolymer is preferably from 40,000 to 200,000.

Examples of the acrylic acid polymer which can be used in the present invention include an acrylic acid homopolymer; copolymers of acrylic acid and vinyl monomers, such as acrylic esters (e.g., butyl acrylate and 2-ethylhexyl acrylate), methacrylic esters (e.g., methyl methacrylate), and vinyl acetate; and other polymers, e.g., a carboxyvinyl polymer. Among these, an acrylic acid polymer having a carboxyl group content of 20% by weight or more is preferred. These polymers may be used either alone or in combinations thereof.

The cellulose derivative which can be used in the present invention must be capable of being dissolved in or swollen with water and a lower alcohol. Examples of the cellulose derivative include methyl cellulose, ethyl cellulose, hydroxyethyl cellulose, hydroxypropyl cellulose, and hydroxypropylmethyl cellulose. The degree of substitution of the cellulose derivative is preferably from 0.1 to 3, and more preferably from 1.0 to 2.5. Hydroxypropyl cellulose having a degree of substitution of from 1.3 to 2.0 is most preferred. These cellulose derivatives may be used either alone or as a mixture of two or more thereof.

A weight ratio of acrylic acid polymer (B) to cellulose derivative (C) (B/C) preferably ranges from 1/9 to 9/1. To ensure further long-term adhesion to the oral mucosa, the weight ratio B/C preferably ranges from 3/7 to 6/4. A weight ratio of vinyl acetate homopolymer (A) to the sum of acrylic acid polymer (B) and cellulose derivative (C) (A/(B+C)) preferably ranges from 2/8 to 8/2. To ensure further long-term adhesion to the oral mucosa, the weight ratio B/C more preferably ranges from 4/6 to 6/4.

Thus, the working time of the preparation in the oral cavity, which partly depends on the duration of adhesion, can be appropriately controlled by varying the ratio of vinyl acetate homopolymer (A), acrylic acid polymer (B), and cellulose derivative (C).

If desired, the adhesive film of the present invention may further contain a salt or a base. That is, since the film comprising only the above-described components assumes acidity attributed to the acrylic acid polymer, it sometimes gives a slight irritation to excitable parts, such as an injured part. Where such an irritation due to acidity gives rise to troubles, incorporation of a salt or base having a neutralizing effect can substantially remove the irritation to the injured part.

Examples of the salts and bases include salts of metals and weak acids, e.g., a salt of an alkali metal (e.g., sodium and potassium) and a carboxylic acid (e.g., acetic acid, lactic acid, and citric acid); metal hydroxides, e.g., sodium hydroxide and potassium hydroxide; amines, e.g., triethanolamine and diisopropanol amine; and mixtures thereof. A salt of an alkali metal (e.g., sodium and potassium) and a carboxylic acid (e.g., acetic acid, lactic acid, and citric acid) is preferably used. The amount of the salt or base to be incorporated widely varies depending on its kind. For example, a monovalent metal salt is preferably used in an amount of from 0.03 to 0.2 equivalent to the acrylic acid polymer. Amounts less than 0.03 equivalent produce insufficient effects to reduce the irritation of an injured part. If the amount exceeds 0.2 equivalent, water resistance of the adhesive film tends to be reduced, failing to attain sufficient adhesion to the oral mucosa.

The film applicable to the oral mucosa according to the present invention can be obtained as follows. A vinyl acetate homopolymer, an acrylic acid polymer, and a cellulose derivative are dissolved in a solvent commonly compatible to them to form a film-forming composition. The composition is cast on a releasable liner and dried to form a film.

Examples of the solvent commonly compatible to the film-forming components include an alcohol and a water-alcohol mixed solvent. Taking solubility of the cellulose derivative into consideration, lower alcohols, e.g., methanol and ethanol, are exemplified as the alcohol. The water content in the mixed solvent is preferably not more than 30% by weight. If it exceeds 30% by weight, the vinyl acetate homopolymer tends to be hardly dissolved.

Examples of the releasable liner on which the film-forming composition is cast includes a release-treated polyethylene laminated paper, a polyethylene film, and a silicone-treated polyethylene terephthalate film.

Drying of the cast film can be carried out in a high-temperature air bath using a drying oven or a drying tower, and a vacuum drier.

Thickness of the film can be adjusted by controlling the amount of the composition cast and is preferably in the range of from 5 to 500 $\mu$m. From the standpoint of film strength and a feeling on use, a thickness of from 10 to 100 $\mu$m is more preferred.

The film applicable to the oral mucosa according to the present invention basically comprises a homogeneous and soft adhesive film which is obtained from a vinyl acetate homopolymer, an acrylic acid polymer, and a cellulose derivative as described above. If desired, a water-insoluble support may be provided on the adhesive film to endow the preparation with improved shape retention on water absorption.

Examples of the water-insoluble support includes a film of a synthetic resin, e.g., polyethylene, a vinyl acetate homopolymer, an ethylene-vinyl acetate copolymer, polyvinyl chloride, and polyurethane; a metal foil, e.g., an aluminum foil and a tin foil; and a laminate film comprising cloth or paper and a synthetic resin film. From the viewpoint of safety and a feeling on use, it is preferable to use a film of a synthetic resin, e.g., polyethylene, a vinyl acetate homopolymer, and an ethylene-vinyl acetate copolymer as a support. In order to assure ease in handling and to avoid giving an adverse feeling on use, the water-insoluble support preferably has a thickness of from 10 to 100 μm.

The above-described composite film can be obtained by, for example, hot pressing the adhesive film and the water-insoluble support film. Alternatively, the composite film can be obtained by casting the above-described film-forming composition on the water-insoluble support followed by drying.

The thus obtained film or composite film according to the present invention, when applied to the wet oral mucosa, absorbs water contents and is swollen with the water contents to exhibit excellent adhesion and shape retention for an extended time without causing an adverse feeling while protecting the site. The film is thus applicable to an affected part in the oral cavity as bandage. Where a drug is used in combination, the drug can be prevented from running off due to saliva, etc., and an administration of the drug to the affected part can be maintained in a stable manner.

The preparation applicable to the oral mucosa according to the present invention is prepared by incorporating a topical drug into the adhesive film. The preparation can be used for the treatment of an affected part in the oral cavity.

Topical drugs which can be used in the preparation of the invention may be either solid or liquid at room temperature, and any topical drug which can be dissolved or dispersed in the soft adhesive film can be employed. The method for dissolving or dispersing the topical drugs in the soft adhesive film is not particularly limited. For example, the vinyl acetate homopolymer, the acrylic acid polymer and the cellulose derivative are dissolved in a solvent which is compatible to these components, and the topical drug is separately dissolved or dispersed in the same solvent. The resulting solutions (or solution and dispersion) are mixed with each other to form a film-forming composition, and the film-forming composition is then cast on a releasable liner followed by drying so as to form the preparation.

Examples of the topical drugs include glucocorticoids, e.g., Triamcinolone Acetonide, Dexamethasone, Betamethasone, Prednisolone, Fluocinolone, Hydrocortisone, Beclomethasone, etc. and salts thereof; antiinflammatory agents, e.g., Flurbiprofen, Ibuprofen, Diclofenac, Indomethacin, Bendazac, Flufenamic Acid, Bufexamac, Cyclosporins, Clidanac, Glycyrrhizin, Ketoprofen, Piroxicam, Pranoprofen, Benzydamine, Ibuprofen Piconol, Etofenamate, Lysozyme, Chymotrypsin, Epidihydrocholesterin, Hinokitiol, α-Amylase, Azulene, Chlorophyllin, Cromoglicic Acid, Tranilast, Serrapeptase, Pronase, Glucanase, *Lithospermi Radix* extract, etc. and salts thereof; bactericides, e.g., Acrinol, Cetylpyridinium, Chlorhexidine, Domiphen, Iodine, Monensin, Sanguinarine, Metronidazole, Dequalinium, Thetracycline, Minocycline, Ofloxacin, Penicillin, Oxycycline, Oxytetracycline, Cefatrizine, Nystatin, Clindamycin, Fradiomycin Sulfate, etc. and salts thereof; analgesics, e.g., Ethyl Aminobenzoate, Camphor, Eugenol, Dibucaine, Phenol, Menthol, Creosote, Diphenhydramine, Lidocaine, Tetracaine, Procaine, Cocaine, Piperocainum, Mepivacaine, Bromoxine, Guaiacol, etc. and salts thereof; hemostatics, e.g., Tranexamic Acid, β-Aminocaproic Acid, Alginic Acid, Bioflavonoid, Vitamin C, Thrombin, Oxidized Cellulose, Cetraxate, Epinephrine, Ferric Chloride, Fibrinogen, Carbazochrome, etc. and salts thereof; vasodilators, e.g., Inositol Hexanicotinate, Cyclandelate, Cinnarizine, Tolazoline., Acetylcholine, etc. and salts thereof; tissue repairing agents, e.g., Solcoseryl, Proglumide, Sucralfate, Nicametate, Gefarnate, Glutamine, Aceglutamide Aluminum, Ethylcysteine, Chitin, Vitamin E Nicotinate, Ubidecarenone, etc. and salts thereof; antiviral agents, e.g., Aciclovir, Idoxuridine, Amantadine, etc. and salts thereof; bone metabolic agents, e.g., Vitamin D, Endotoxin, Hydroxyapatite, Collagen, Cataboline, 2-Chloroadenosine, Mecardia, Calcitriol, prostaglandins for the alveolar bone, parathyroid hormone for the alveolar bone, Calcitonin for the alveolar bone, etc. and salts thereof; and astringents, e.g., Tannin, Tannic Acid, zinc bromide, sodium fluoride, strontium fluoride, potassium nitrate, tin fluoride, aluminum potassium sulfate, Berberine, bismuth derivatives, strontium fluoride, aluminum lactate, etc. and salts thereof.

The amount of the topical drug to be incorporated into the adhesive film depends on the kind of the drug and is generally selected from 0.001 to 40% by weight, preferably from 0.002 to 20% by weight, based on the film in view of the pharmacological effects and adhesion to the oral mucosa.

The preparation applicable to the oral mucosa according to the present invention is less causative of an adverse feeling on use, excellent in shape retention on water absorption, and adhesive to the oral mucosa for an extended period of time, thereby maintaining a stable administration of a topical drug.

As described above, the film or preparation applicable to the oral mucosa of the present invention which comprises a soft adhesive film prepared from a homogeneous mixture of a vinyl acetate homopolymer, an acrylic acid polymer, and a specific cellulose derivative is soft, less causative of an adverse feeling in the oral cavity on use and excellent in shape retention on water absorption. Further, the film or preparation exhibits close adhesion to the oral mucosa for a long period of time. Furthermore, because of the homogeneity and softness, the film or preparation can be deformed in perfect accord with the shape of the oral mucosa simply by lightly pressing and adhered close to the mucosa.

The present invention is now illustrated in greater detail by way of the following Examples, but it should be understood that the present invention is not deemed to be limited thereto. In these examples, all the parts, percents and ratios are by weight unless otherwise specified.

EXAMPLE 1

Five parts of a vinyl acetate homopolymer (weight average molecular weight: 172,000), 3 parts of a carboxyvinyl polymer (carboxyl group content: 58–63% by weight) (as the acrylic acid polymer), 2 parts of hydroxypropyl cellulose (viscosity: 6.0-10.0 cp (2%-aqueous solution at 20° C.)) (as the cellulose derivative) were added to 90-parts of a 1/9 water/methanol mixture as a common solvent to form a film-forming composition. The composition was cast over a silicone-release paper, dried, and stripped off to obtain a 30 μm thick adhesive film.

COMPARATIVE EXAMPLE 1

Five parts of a vinyl acetate homopolymer (weight average molecular weight: 172,000) and 5 parts of a hydroxypropyl cellulose (viscosity: 6.0-10.0 cp (2%-aqueous solution at 20° C.)) (as the cellulose derivative) were added to 90 parts of a 1/9 water/methanol mixture as a common solvent to form a film-forming composition. The composition was cast over a silicone-release paper, dried, and stripped off to obtain a 30 μm thick film.

Each of the films prepared in Example 1 and Comparative Example 1 was observed under an optical microscope. The three components constituting the film of Example 1 were found homogeneously mixed together, and each of them did not exist solely in parts, whereas the two components constituting the film of Comparative Example 1 were not homogeneously mixed and each of them solely existed in parts.

EXAMPLE 2

A 30 μm thick soft sheet of a vinyl acetate homopolymer (weight average molecular weight: 129,000) was laminated as a water-insoluble support on a side of the film obtained in Example 1 by hot pressing to obtain a composite film applicable to the oral mucosa.

COMPARATIVE EXAMPLE 2

Five parts of a vinyl acetate homopolymer (weight average molecular weight: 172,000) and 5 parts of a carboxyvinyl polymer (carboxyl group content: 58-63% by weight) (as the acrylic acid polymer) were added to 90 parts of a 1/9 water/methanol mixture as a common solvent to prepare a film-forming composition. The composition was cast on a silicone-release paper, dried, and stripped off to obtain a 30 μm thick film. A 30 μm thick soft sheet of a vinyl acetate homopolymer (weight average molecular weight: 129,000) as a water-insoluble support was hot-pressed on the film to obtain a composite film.

COMPARATIVE EXAMPLE 3

Five parts of a carboxyvinyl polymer (carboxyl group content: 58-63% by weight) (as the acrylic acid polymer) and 5 parts of hydroxypropyl cellulose (viscosity: 6.0-10.0 cp (2%-aqueous solution at 20° C.)) (as the cellulose derivative) were added to 90 parts of a 1/9 water/methanol mixture as a common solvent to prepare a film-forming composition. The composition was cast on a silicone-release paper, dried, and stripped off to obtain a 30 μm thick film. A 30 μm thick soft sheet of a vinyl acetate homopolymer (weight average molecular weight: 129,000) as a water-insoluble support was hot-pressed on the film to obtain a composite film.

Adhesion of each of the composite films prepared in Example 2 and Comparative Examples 2 and 3 was evaluated according to the following test method (Test A), and the results obtained are shown in Table 1 below.

Test A:

A circular specimen of 10 mm in diameter was cut out of the composite film. The adhesive layer of the specimen was adhered to a water-swollen crosslinked collagen film fixed on a phenolic resin plate and soaked in water at 37° C. under stirring at a constant speed. The time required for the film to spontaneously come off the collagen film was measured. The measurement was conducted on 5 specimens for each sample, and the results were averaged.

TABLE 1

|  | Example 2 | Comparative Example 2 | Comparative Example 3 |
| --- | --- | --- | --- |
| Time of adhesion (min) | 422 ± 4 | 162 ± 3 | 28 ± 3 |

EXAMPLE 3

Five parts of a vinyl acetate homopolymer (weight average molecular weight: 129,000), 2 parts of a carboxyvinyl polymer (carboxyl group content: 58-63% by weight) (as the acrylic acid polymer), 3 parts of hydroxypropylmethyl cellulose (degree of substitution: 1.86-1.90) (as the cellulose derivative), and 0.1 part of sodium citrate (as the salt neutralizing the acrylic acid polymer) were added to 90 parts of a 1/9 water/methanol mixture as a common solvent to prepare a film-forming composition. The composition was cast on a silicone-release paper, dried, and stripped off to obtain a 30 μm thick adhesive film. A 30 μm thick soft sheet of a vinyl acetate homopolymer (weight average molecular weight: 155,000) as a water-insoluble support was hot-pressed on the adhesive film to obtain a composite film applicable to the oral mucosa.

Shape retention of the composite film of Example 3 was evaluated according to the following test method (Test B), and the results obtained are shown in Table 2 below.

TEST B

A 1 cm × 2 cm specimen was cut out of the film. The adhesive layer of the specimen was applied to the gingiva of the upper jaw of each of 10 panel members after wiping off the saliva. After the application for 24 hours, the adhered area of the film was determined visually. During the test, the panel members continued their daily life, such as taking foods, drinks, etc.

TABLE 2

| Panel member | Time of adhesion (hour) | Area of adhesion (%) |
| --- | --- | --- |
| A | 24 | 50 |
| B | 24 | 100 |
| C | 24 | 80 |
| D | 24 | 100 |
| E | 24 | 100 |
| F | 24 | 100 |
| G | 24 | 90 |
| H | 24 | 100 |
| I | 24 | 100 |
| J | 24 | 100 |
| Average |  | 92 |

As shown in Table 2, the average area of adhesion after the application for 24 hours was 92%.

Further, the sample of Example 3 was tested for an adverse feeling in the oral cavity on use according to the following test method (Test C).

TEST C

A specimen of 1 cm × 2 cm cut out of the sample was applied to the gingiva of the upper jaw of 10 panel members, and the feeling was judged according to the following rating system. For comparison, a commercially available track-field type tablet of Sodium Gualenate (Azunol ST made by Nippon Shinyaku Co., Ltd.) was inserted to the same site, and the feeling was judged.

TABLE 3

| Panel Member | Example 3 | Sample of Azunol ST |
|---|---|---|
| 1 | 1 | 3 |
| 2 | 1 | 3 |
| 3 | 1 | 4 |
| 4 | 2 | 4 |
| 5 | 1 | 4 |
| 6 | 1 | 3 |
| 7 | 2 | 4 |
| 8 | 1 | 4 |
| 9 | 1 | 4 |
| 10 | 1 | 3 |

Rating System:
1 No adverse feeling
2 Slight adverse feeling
3 Adverse feeling
4 Considerable adverse feeling From the results of Table 3, the sample of Example 3 was rated 1.2 in average, while Axunol ST was rated 3.6 in average. It can thus be seen that the film of Example 3 causes substantially no adverse feeling in the oral cavity on use.

EXAMPLE 4

Five parts of a vinyl acetate homopolymer (weight average molecular weight: 69,000), 2 parts of polyacrylic acid (as the acrylic acid polymer; molecular weight: 5,000), 3 parts of hydroxypropylmethyl cellulose.(degree of substitution: 1.86-1.90) (as the cellulose derivative), and 0.1 part of Triamcinolone Acetonide (as the topical drug) were added to 90 parts of a 1/9 water/methanol mixture as a common solvent to prepare a film-forming composition. The composition was cast on a silicone-release paper, dried, and stripped off to obtain a 30 μm thick adhesive film. A 20 μm thick soft aluminum foil was hot-pressed as a water-soluble support on the resulting adhesive film to obtain a composite film preparation applicable to the oral mucosa.

Adhesion of the resulting preparation to the oral mucosa was evaluated according to the following test method (Test D).

TEST D

Prior to testing, an agar gel as a substitute for the oral mucosa was prepared as follows.

Distilled water was added to 2 g of agar powder (Japanese Pharmacopeia) to make 100 g and boiled to completely dissolve the agar. The agar solution was put in a dish and allowed to cool to prepare an agar gel.

A specimen of 1 cm × 2 cm cut out of the preparation of Example 4 was adhered to the surface of the agar gel. After a prescribed period of time, the specimen was recovered and extracted from 50 ml of methanol. The drug in the extract was determined by high performance liquid chromatography. The results obtained were plotted against time as shown in FIG. 1.

FIG. 1 reveals that the preparation of Example 4 keeps adhered to the agar gel, a substitute for the oral mucosa, for an extended period of time, releasing the active ingredient with time.

While the invention has been described in detail and with reference to specific embodiments thereof, it will be apparent to one skilled in the art that various changes and modifications can be made therein without departing from the spirit and scope thereof.

What is claimed is:

1. A film applicable to the oral mucosa, comprising a homogenous mixture comprising
    (a) a vinyl acetate homopolymer,
    (b) an acrylic acid polymer, and
    (c) a cellulose derivative capable of being dissolved in or swollen with water and a lower alcohol, wherein said film further contains a salt or base neutralizing said acrylic acid polymer,
        wherein said salt or base is present in an amount of from 0.03 to 0.2 equivalent to said acrylic acid polymer,
wherein said acrylic acid polymer and cellulose derivative are present at a weight ratio from 1/9 to 9/1, and wherein the lower alcohol is methanol or ethanol.

2. A film as claimed in claim 1, wherein said cellulose derivative is selected from the group consisting of methyl cellulose, ethyl cellulose, hydroxyethyl cellulose, hydroxypropyl cellulose and hydroxypropylmethyl cellulose.

3. A film as claimed in claim 1, wherein said acrylic acid polymer and cellulose derivative are present at a weight ratio of from 3/7 to 6/4.

4. A film applicable to the oral mucosa, comprising a homogenous mixture comprising
    (a) a vinyl acetate homopolymer,
    (b) an acrylic acid polymer, and
    (c) a cellulose derivative capable of being dissolved in or swollen with water and a lower alcohol, wherein said film further contains a salt or base neutralizing said acrylic acid polymer,
        wherein said salt or base is present in an amount of from 0.03 to 0.2 equivalent to said acrylic acid polymer,
wherein the weight ratio of said vinyl acetate homopolymer to the sum of said acrylic acid polymer and cellulose derivative is from 2/8 to 8/2, and wherein the lower alcohol is a methanol or ethanol.

5. A film as claimed in claim 4, wherein said acrylic acid polymer and cellulose derivative are present at a weight ratio of from 4/6 to 6/4.

6. A film as claimed in claim 1, wherein said adhesive film has a thickness of from 5 to 500 μm.

7. A film as claimed in claim 1, wherein said film has a water-insoluble soft film support laminated on a side thereof.

8. A film as claimed in claim 7, wherein said support has a thickness of from 10 to 100 μm.

9. A film as claimed in claim 7, wherein said support is a polyethylene film, a vinyl acetate homopolymer film or an ethylene-vinyl acetate copolymer film.

* * * * *